United States Patent [19]
Kameda et al.

[11] Patent Number: 5,393,500
[45] Date of Patent: Feb. 28, 1995

[54] APPARATUS FOR TREATING INFECTIOUS MEDICAL WASTES WITH MICROWAVES AND HOT AIR

[75] Inventors: Takashi Kameda; Shigenori Kataoka; Koichi Noma, all of Kobe, Japan

[73] Assignee: Kawasaki Jukogyo Kabushiki Kaisha, Kobe, Japan

[21] Appl. No.: 27,797

[22] Filed: Mar. 8, 1993

Related U.S. Application Data

[63] Continuation of Ser. No. 827,620, Jan. 29, 1992, Pat. No. 5,322,603.

[30] Foreign Application Priority Data

| | | | |
|---|---|---|---|
| Jul. 11, 1991 | [JP] | Japan | 3-197162 |
| Jul. 11, 1991 | [JP] | Japan | 3-197163 |
| Jul. 16, 1991 | [JP] | Japan | 3-201235 |
| Jul. 18, 1991 | [JP] | Japan | 3-203456 |

[51] Int. Cl.$^6$ ............................................. B01J 19/02
[52] U.S. Cl. ................... 422/186; 204/157.43; 422/21; 588/212; 588/214
[58] Field of Search .................. 422/21, 186; 204/157.43; 588/212, 214

[56] References Cited

U.S. PATENT DOCUMENTS 5,213,758 5/1993 Kawashima et al. ............... 422/21

Primary Examiner—Daniel D. Wasil
Assistant Examiner—Daniel Jenkins
Attorney, Agent, or Firm—Leydig, Voit & Mayer

[57] ABSTRACT

There is disclosed a method of treating medical wastes composed mainly of plastics materials, in which microwaves are applied to the medical wastes, and also circulating hot air is applied to the medical wastes, and preferably the microwaves are applied to the medical wastes in a concentrated manner during an initial stage of the treatment at which water contained in the medical wastes is heated and mostly evaporated. Apparatus for performing this treatment method includes a sealed apparatus body having a medical waste introduction door and hot air outlet and inlet and, a medical waste receiving vessel for being received in the sealed apparatus body, and a hot air circulating line interconnecting the hot air outlet and inlet and the circulating line has a hot air heater and a hot air circulating blower.

10 Claims, 5 Drawing Sheets

APPARATUS FOR TREATING INFECTIOUS MEDICAL WASTES WITH MICROWAVES AND HOT AIR

This application is a continuation of application Ser. No. 07/827,620, filed Jan. 29, 1992, now U.S. Pat. No. 5,322,603.

BACKGROUND OF THE INVENTION

This invention relates to an apparatus for efficiently effecting the sterilization and volume-reduction treatments of infectious medical wastes such as a used hemodialyzer, a used syringe, a used syringe needle, a used gauze and a used container.

In order to prevent the secondary infection caused by infectious medical wastes discharged from hospitals, dialysis facilities and the like, the Japanese Welfare Ministry announced, on Nov. 7, 1989, the guidelines on methods of treating such wastes, and these regulations have been put into force from Apr. 1, 1990. Therefore, in principle, the hospitals, the dialysis facilities and the like have the obligation to sterilize the infectious medical wastes in their facilities.

It has been thought that, for example, steam, a band heater, hot air circulation, and a high-frequency generator could be used for heating and sterilizing the infectious medical wastes.

Referring to the prior art, Japanese Patent Unexamined Publication No. 1-176486 discloses a treatment method and a treatment apparatus in which used syringes of a synthetic resin and used syringe needles are put into a heat-resistant vessel, and these wastes are heated to a predetermined temperature and melted by an electric heater or heaters and a far infrared heater or heaters, thereby sterilizing them, and then the molten wastes are cooled and solidified.

Japanese Utility Model Unexamined Publication No. 1-144040 discloses an apparatus for heating and sterilizing wastes in which the wastes are heated and sterilized by hot air, and then the wastes are crushed and reduced in volume by a crusher.

Japanese Patent Publication No. 51-25470 discloses an apparatus for treating plastic wastes in which the plastic wastes received within a cylinder are heated by heaters contained in a bottom plate and a piston, and are melted mainly at the surfaces of these wastes simultaneously with the compression of the wastes, to thereby mold them into an integral block.

Japanese Patent Unexamined Publication No. 1-315383 discloses an apparatus in which used disposable syringes are heated and sterilized by an electric heater or heaters and a far infrared heater or heaters mounted on a side wall or walls and/or a bottom wall of a heating furnace. Also, this publication discloses, as one embodiment, a method in which wastes to be treated are melted in a heat-resistant vessel, and then are cooled and solidified into an integral block containing needles, and thereafter this integral block is taken out.

Japanese Patent Unexamined Publication No. 1-263410 discloses an apparatus in which wastes are heated by microwaves to be dried and burnt into ashes.

Problems with the steam heating are the production of waste water and a legal limitation on a pressure vessel. The heating by the band heater or the like causes a local overheating which adversely affects a heat transfer efficiency. As regards the heating by the hot air circulation, a satisfactory heat transfer is not obtained merely by blowing a blast of hot air, which may cause local overheating. The high-frequency heating has a problem in that particularly after the evaporation of water, a local overheating may occur because of the difference in selectivity of the high-frequency absorption by the materials.

Relatively small medical wastes, such as a syringe, can be sufficiently treated by hot air circulation or the band heater, and also the high-frequency heating can be effectively used for incinerating medical wastes. However, for treating large-size medical wastes, such as a hemodialysis instrument which is composed mainly of plastic materials containing polyvinyl chloride, and contains a large amount of water therein, these treatment means have both merits and demerits, and are not suitable. When the medical waste containing polyvinyl chloride is incinerated or subjected to a local overheating, there is a possibility that poisonous gas such as hydrogen chloride may be produced.

Particularly when a large-size hemodialyzer, composed of several kinds of plastic materials of different melting points, is treated by the use of the treatment method and apparatus disclosed in the above Japanese Patent Unexamined Publication No. 1-176486, many portions of the hemodialyzer remain unmelted depending on the treatment temperature, and therefore the volume reduction (molding) is inadequate. Also, the large-size waste, such as a hemodialyzer, is liable to undergo a local overheating because of the use of the electric heater and the far infrared heater, and therefore there is a possibility that poisonous gas, such as hydrogen chloride gas, may be produced from polyvinyl chloride.

In the crushing method performed by the crusher in the apparatus for heating and sterilizing wastes, disclosed in the above Japanese Utility Model Unexamined Publication No. 1-144040, the volume reduction effect is not always satisfactory, and besides the maintenance of the cutter of the crusher is necessary, and also noises and vibrations are large, and many power sources are needed.

In the apparatus for treating plastic wastes, disclosed in the above Japanese Patent Publication No. 51-25470, sterilization is not intended at all, and the concept disclosed in this publication is to coat only the surface of the wastes with the molten material, and therefore there is a disadvantage that the stability of the molded block is unsatisfactory.

When a large-size waste, such as a used hemodialyzer containing water therein, is treated by the apparatus disclosed in the above Japanese Patent Unexamined Publication No. 1-315383, the temperature of the waste can not rise easily only by hot air circulation, and the sterilization is not satisfactory, and the treatment time is long. In addition, since the hemodialyzer is composed of a plurality of kinds of plastic materials, some of these plastic materials become molten while the others do not become molten, depending on the treatment temperature, so that the volume reduction can not be effected adequately.

When a waste such as a used hemodialyzer, or a waste comprising various tubes of different plastic materials, is treated by the apparatus disclosed in the above Japanese Patent Unexamined Publication No. 1-263410, a large amount of poisonous gas such as hydrogen chloride is produced. Therefore, consideration must be given to the material of the apparatus, and besides an exhaust gas treatment device of a large volume is needed for dealing with the exhaust gas. This complicates the construction of the treatment apparatus, and increases the size thereof. Further, in the method in which the ashing is carried out by microwaves so as to effect the volume reduction, much electric power is required, and the apparatus itself is heated to elevated temperatures, and therefore this apparatus can not suitably be installed in a hospital or a clinic.

In the conventional treatment apparatus using microwaves, since the microwaves are applied to the whole of the heating chamber, much of the microwave energy is wasted, and therefore the efficiencies of the heating, sterilization and volume reduction of the waste to be treated are not good. In addition to these disadvantages, there exists another problem that a door of the heating chamber is complicated in construction in order to prevent the leakage of the microwaves from the apparatus and also to maintain the airtightness of the heating chamber.

The infectious medical wastes contain a plurality of kinds of plastic materials. For example, when the material ratio of one set of waste dialysis instruments, including a hemodialyzer, a blood circuit (including tubes and etc.), a syringe and a physiological salt solution vessel, was analyzed, the following results were obtained:

| (1) Polyvinyl chloride | 50 wt. % |
|---|---|
| (2) Polystyrene or polycarbonate | 30 wt. % |
| (3) Cellulose or synthetic membrane | 5 wt. % |
| (4) Polyethylene, or polypropylene, or silicone | 5 wt. % |
| (5) Polyurethane and stainless steel | 10 wt. % |

Incidentally, the natures of the main plastic materials among the above materials are shown in Table 1 below.

TABLE 1

| Kind of material | Melting point | Softening point | Notes |
|---|---|---|---|
| Polyvinyl chloride | about 170° C. | 65 to 85° C. | HCl gas is produced at above 190° C. |
| Polystyrene | about 230° C. | 90 to 102° C. | Deformation temperature: 70 to 100° C. (ASTM D648) Softening point: 97 to 100° C. (ASTM D1525 - 58T) |
| Polycarbonate | about 230 to 260° C. | 145 to 165° C. | Deformation temperature (ASTM D648) 130 to 136° C. (18.6 kg/cm$^2$) 136 to 142° C. (4.6 kg/cm$^2$) |
| (medium-density) Polyethylene | about 120° C. | | Softening temperature: about 100 to 120° C. (ASTM D1525) Deformation temperature: 50 to 66° C. (ASTM D648) |
| Polypropylene | about 170° C. | 96 to 105° C. (ASTM D1525) | |

Remarks: ASTM (American Society of Testing Material)

SUMMARY OF THE INVENTION

With the above deficiencies of the prior art in view, it is an object of this invention to provide a method and an apparatus which can effectively treat infectious medical wastes.

According to one aspect of the present invention, there is provided a method of treating medical wastes composed mainly of plastic materials, comprising the step of applying microwaves to the medical wastes and applying circulating hot air to the medical wastes to thereby heat and sterilize the medical wastes.

Preferably, the microwaves are applied to the medical wastes in a concentrated manner during an initial stage of the treatment at which water contained in the medical wastes is heated and completely evaporated. By doing so, the medical wastes can be treated more effectively.

According to another aspect of the invention, there is provided apparatus for treating medical wastes which comprises a sealed apparatus body having an introduction door, a hot air outlet and a hot air inlet; a microwave generating device connected to the sealed apparatus body; and a hot air circulating portion interconnecting the hot air outlet and the hot air inlet, the hot air circulating portion having a hot air heater and a hot air circulating blower.

According to a further aspect of the invention, there is provided apparatus for treating medical wastes which comprises a sealable heating chamber having an introduction door, a hot air outlet and a hot air inlet; a waste receiving vessel disposed in the heating chamber, the waste receiving vessel having hot air passage holes; a microwave generating device connected to the heating chamber; a hot air circulating portion interconnecting the hot air outlet and the hot air inlet, the hot air circulating portion having a hot air heater and a hot air circulating blower; a seal or sealing plate provided at an opening of the waste receiving vessel so as to seal the waste receiving vessel, the seal plate having a hot air inlet port for effectively introducing the hot air into the waste receiving vessel; a seal plate moving device for moving the seal plate; and a hot air introduction device interconnecting the hot air inlet of the heating chamber and the hot air inlet port of the waste receiving vessel.

A partition wall may be provided to extend between the peripheral wall of the waste receiving vessel and the peripheral wall of the heating chamber.

DESCRIPTION OF THE PREFERRED EMBODIMENTS

Preferred embodiments of the present invention will now be described with reference to the drawings. The shapes of constituent devices in these embodiments, as well as the arrangement of these devices relative to one another, are given not in a limitative sense, but merely by way of example unless specifically described to that effect.

Figure 1:
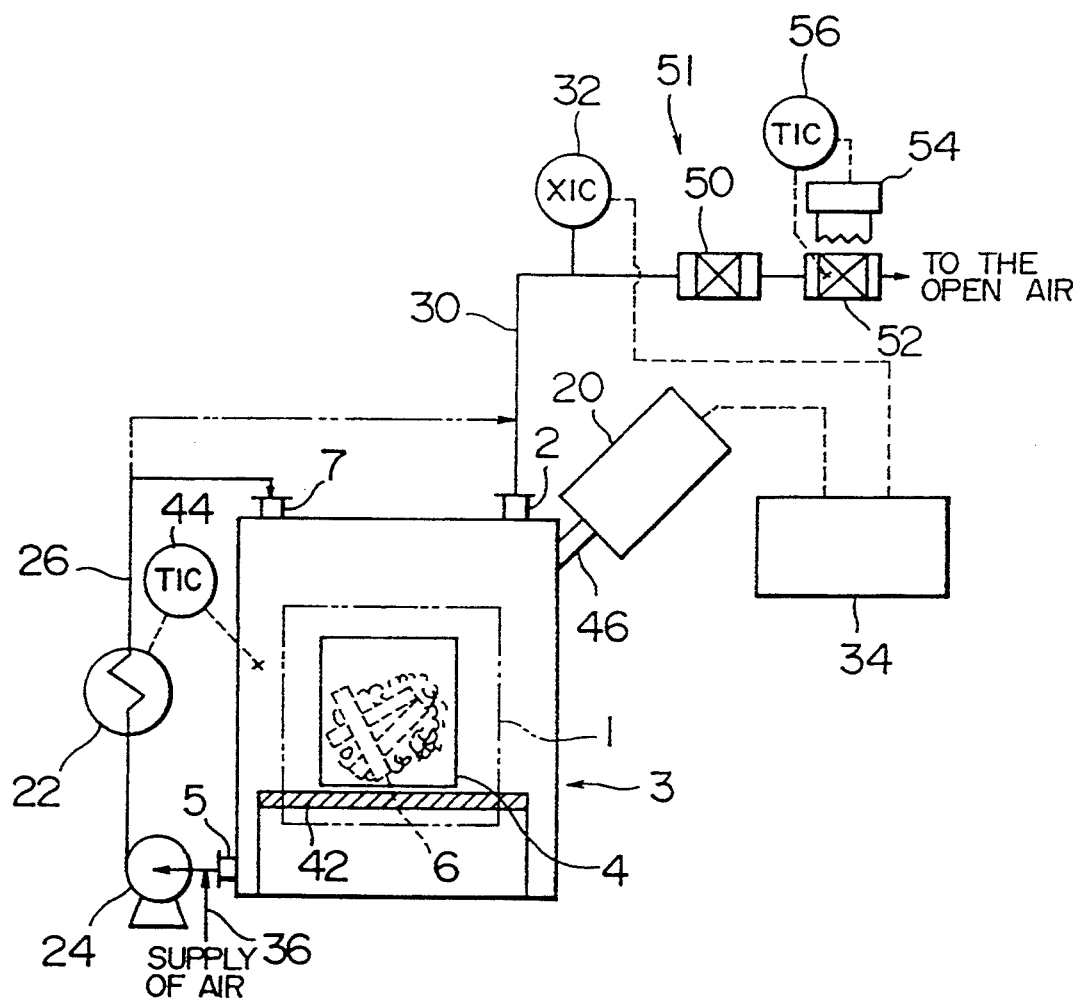
FIG. 1 is a schematic view of a medical waste treatment apparatus according to one preferred embodiment of the present invention.

FIG. 1 shows one embodiment of the invention in which the judgment of evaporation of water is made based on a hydrogen chloride gas concentration, a combustible gas concentration, a water concentration, or an odor component concentration in an exhaust gas.

As shown in FIG. 1, a medical waste treatment apparatus of this embodiment comprises a sealed apparatus body (heating chamber) 3 having an introduction door 1, an exhaust port 2, a hot air outlet 5 and a hot air inlet 7, a medical waste-receiving vessel 4, a microwave generating device 20, a hot air circulating line 26 having a hot air heater 22 and a hot air circulating blower 24, an indicating controller 32 for the hydrogen chloride gas concentration, the combustible gas concentration, the water concentration or the odor component concentration, which indicating controller 32 is mounted on an exhaust gas conduit 30, and a control unit 34 for controlling the microwave generating device 20 in accordance with the concentration of the hydrogen chloride gas, the combustible gas, the water or the odor component. Reference numeral 36 denotes an intake tube (or an intake opening) for supplying the atmosphere into the system, reference numeral 42 a bottom plate, reference numeral 44 a temperature indicating controller, and reference numeral 46 a waveguide. Instead of connecting the exhaust gas conduit 30 to the exhaust port 2, this exhaust gas conduit 30 may be connected to the hot air circulating line 26 as indicated by a two dots-and-dash line in FIG. 1. Also, the waveguide 46 may be omitted in which case the microwave generating device 20 is connected directly to the sealed apparatus body 3. Further, instead of the hot air circulating line 26, there can be used a double heating chamber structure (e.g. a double shell structure) having a hot air flow passage having the same function as that of a piping.

An exhaust gas treatment device 51 is provided on the exhaust gas conduit 30. This treatment device 51 comprises an alkali filling portion 50 for removing acid gas such as HCl, and a catalyst filling portion 52 filled with an oxidizing catalyst e.g. alumina-carried platinum or palladium catalyst, which oxidizes hydrocarbon and converts it into water and $CO_2$, and removes the odor components, and prevents the dissipation of germs. The order of arrangement of these portions 50 and 52 in FIG. 1 is given merely as one example, and can be suitably changed. Reference numeral 54 denotes a heater, and reference numeral 56 denotes a temperature indicating controller. A fan may be mounted on the exhaust gas conduit, and by doing so, the heating chamber and the hot air circulating line can be entirely operated by a negative pressure, thereby preventing the gas, containing the germs, from leaking to the outside of the system.

The exhaust gas treatment device 51 adsorbs and removes the acid gas, such as hydrogen chloride gas, at a reaction adsorption temperature of 150° to 200° C. (preferably, 170° to 180° C.) at a space velocity of 500 to 5000 $hr^{-1}$ (preferably, 1000 to 2000 $hr^{-1}$), using a reaction adsorbent selected from the group consisting of oxides and hydroxides (e.g. $Na_2O$, $CuO$, $Fe_2O_3$) of the elements in groups I, II and VIII of the periodic table. Also, the exhaust gas treatment device 51 effects the oxidative decomposition of the combustible gas and the odoriferous gas at a reaction temperature of 200° to 450° C. (preferably, 350° to 420° C.) at a space velocity of 500 to 40,000 $hr^{-1}$ (preferably, 1000 to 10,000 $hr^{-1}$), using a Pt and/or Pd catalyst. A suitable amount of the Pt or Pd in the catalyst is 0.2 to 2.0 wt.% and preferably 0.5 wt.%.

For using the above apparatus, medical wastes 6 are put into the medical waste receiving vessel 4, and this vessel 4 is introduced into the sealed apparatus body 3. Then, the microwave generating device 20 is operated to heat and evaporate the water contained in the medical wastes 6 received in the vessel 4, and at the same time the hot air is circulated by the hot air circulating line 26 having the hot air heater 22 and the hot air circulating blower 24, thereby heating and sterilizing the medical wastes 6. The microwave generating device 20 is controlled by detecting the water concentration, the odor component concentration, the combustible gas concentration or the hydrogen chloride gas concentration, or by detecting the incident-reflective electric power ratio by a power monitor. For example, the microwave generating device 20 is controlled by detecting the combustible gas concentration, the hydrogen chloride gas concentration, the water concentration or the odor component concentration in the exhaust gas from the sealed apparatus body 3, and/or by detecting the ratio of the reflective electric power to the incident electric power by the power monitor 60 connected to the waveguide 46 of the microwave generating device 20. Also, the microwaves may be applied for a predetermined time period set by a timer.

Next, results of tests conducted using the apparatus of FIG. 1 will be described.

In an inoperative condition of the microwave generating device 20, 20 sets of used hemodialysis instruments were heated to such a temperature as to completely sterilize them, by circulating the hot air of 180° C. The time required for this was 6 to 7 hours.

Similarly, in an operative condition of the microwave generating device 20, 20 sets of used hemodialysis instruments were heated to such a temperature as to completely sterilize them, by circulating the hot air of 180° C. The time required for this was 5 hours.

As will be appreciated from the above results, with the method of the present invention, the time required for the heating to achieve the complete sterilization could be shortened 1 to 2 hours.

When the medical wastes were treated only by microwaves, the microwaves were selectively absorbed particularly by vinyl chloride among the plastic materials constituting the wastes to be treated, and as a result a large amount of hydrogen chloride gas was produced, and also the wastes treated were blackened, that is, scorched.

When the medical wastes were treated by the method of the present invention, the volume of the treated wastes was reduced to about ⅓ of the volume of the wastes before the treatment. Also, during the treatment operation, the concentration of the poisonous gas, such as hydrogen chloride gas and carbon monoxide was at such a level that the poisonous gas was hardly detected. Further, the blackening of the treated wastes was hardly recognized.

In the above method, at the initial stage of the treatment, that is, until the water contained in the medical wastes is heated and completely evaporated, the microwaves are preferably applied in a concentrated manner. Then, preferably, the hot air circulation is used for heating the wastes to the sterilization temperature after the evaporation of the water.

The hot air circulating temperature is 140° to 200° C., and preferably 170° to 180° C. If this temperature is less than 140° C., the sterilization and the volume reduction are insufficient. On the other hand, if this temperature exceeds 200° C., this is suited for the sterilization and volume reduction, but invites the production of a large amount of poisonous gas such as hydrogen chloride, which is not desirable.

In the above method, in order that the steam, the combustible gas components and the poisonous gas components, produced by the heating treatment of the medical wastes, can be prevented from being accumulated in the system, part of the gases is preferably exhausted from the system, while replenishing the atmosphere in the system.

There are two exhaust methods. Namely, one uses the pressure of the hot air circulating blower, and the other uses an exhaust fan. In the former method, the pressure in some portions of the system is positive whereas in the latter method, the pressure in the whole of the system can be made negative. Therefore, the latter method is effective in preventing the gas, containing the odoriferous components and the germs, from leaking to the outside of the system, and also advantageously, fresh air can be replenished by suction into the system merely by providing a nozzle or an opening.

As described above, in the embodiment shown in FIG. 1, since the microwaves are selectively absorbed by the water, the heating and evaporation of the water contained in the wastes can be effected rapidly, and therefore the sterilization treatment can be carried out in a short time. And besides, since the heating is effected by the microwaves and the hot air, the evaporated water is discharged to the outside of the system, together with the exhaust gas, and therefore any waste water is not produced at all.

Further, at the initial stage of the treatment, that is, until the water in the medical wastes is heated and completely evaporated, the microwaves are applied in a concentrated manner, and the heating to the sterilization temperature after the evaporation of the water is effected mainly by the hot air circulation. Therefore, a local overheating can be suppressed relatively easily, and even if such a local overheating occurs, the generation of poisonous gas can be easily suppressed by controlling the temperature of the hot air. Further, by heating the plastic materials contained in the medical waste to temperatures near their softening temperature, the plastic materials themselves are subjected to heat shrinkage, so that the volume can be reduced to about ⅓ of the volume before the treatment. Further, by exhausting the gas from the system and by replenishing the atmosphere in the system, condensation of water and poisonous gas in the apparatus can be prevented, thereby suppressing the corrosion of the apparatus. In the case of providing the fan in the exhaust gas conduit so as to keep the whole of the system under atmospheric pressure, the gas containing the germs can be prevented from leaking to the outside of the system.

Next, another embodiment of the present invention will be described with reference to FIGS. 2 to 5.

Figure 2:
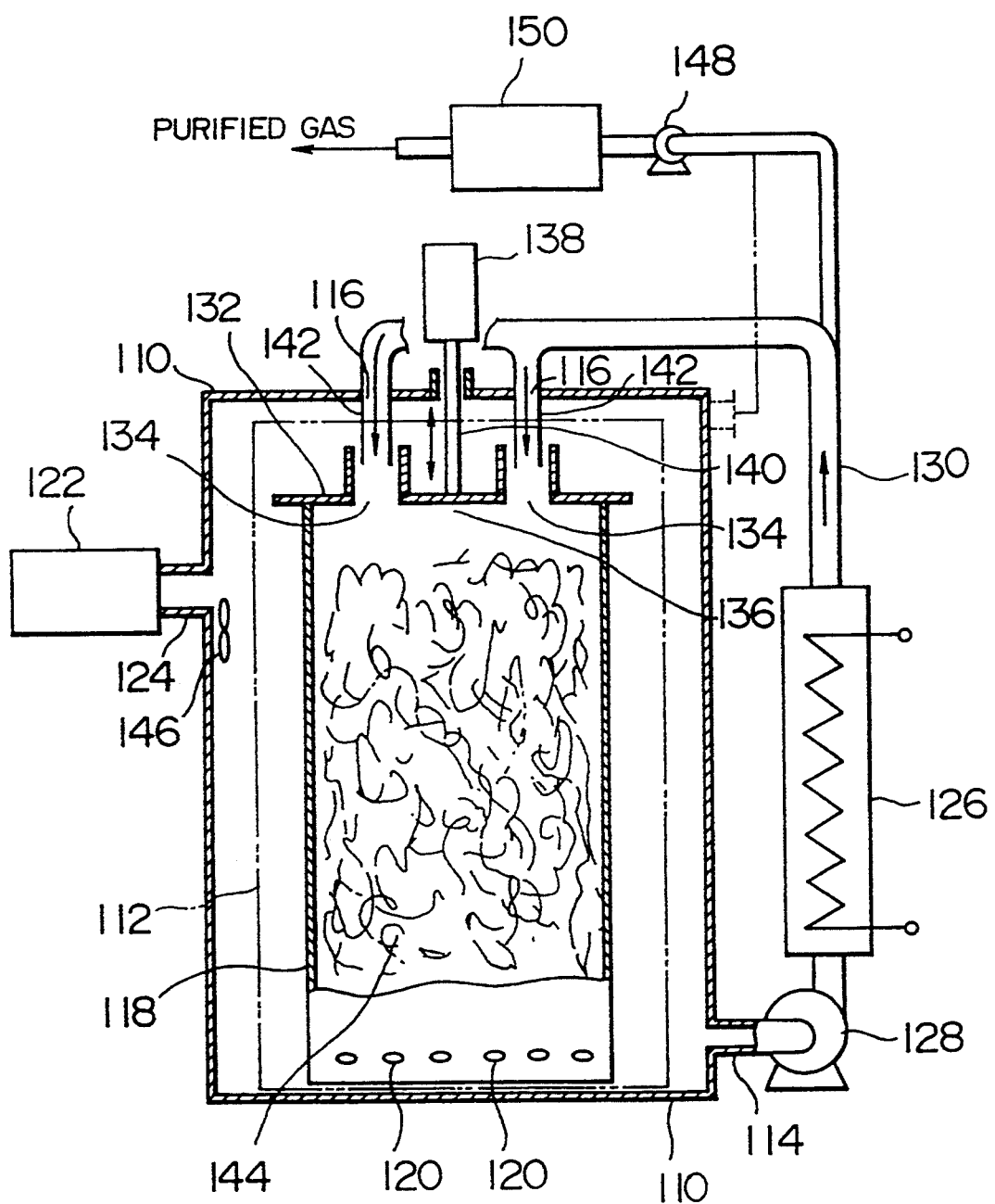
FIG. 2 is a vertical, partly cross-sectional view of a medical waste treatment apparatus according to another embodiment of the invention.

Referring to FIG. 2, a heating chamber 110 which can be sealed has an introduction door 112, a hot air outlet 114 at its lower portion, and hot air inlets 116 at its upper portion. A waste receiving vessel 118 is made of a heat-resistant plastic material or the like allowing microwaves to easily transmit therethrough. This vessel 118 has a number of hot air passage holes 120 at its lower end portion. A microwave generating device 122 is connected to the heating chamber 110 via a waveguide 124. The waveguide 124 may be omitted, in which case the microwave generating device 122 is connected directly to the heating chamber 110. The hot air outlet 114 and the hot air inlets 116 are interconnected by a hot air circulating duct 130 having a hot air heat 126 and a hot air circulating blower 128. Instead of the hot air circulating duct 30, there can be used a double heating chamber structure (e.g. a double shell structure) having the function of a similar hot air flow passage.

A seal or sealing plate 132 for sealing the waste receiving vessel 118 has hot air inlet ports 134, and is disposed in the vicinity of an opening 136 of the waste receiving vessel 118. A seal plate moving device 138 for moving the seal plate 132 upward and downward is connected to the seal plate 132 via a piston 140. The hot air inlets 116 of the heating chamber 110 are connected respectively to the hot air inlet ports 134 of the seal plate 132 by hot air introduction means 142. Reference numeral 144 denotes matters to be treated (medical wastes), reference numeral 146 a stirrer fan for dispersing microwaves uniformly, reference numeral 148 an induced draft fan, and reference numeral 150 an exhaust gas treatment device. The induced draft fan may be omitted. The exhaust gas inlet side of the exhaust gas treatment device 150 is connected to the hot air circulating duct 130, but may be connected to the upper portion of the heating chamber as indicated by a two dots-and-dash line.

Figure 3:
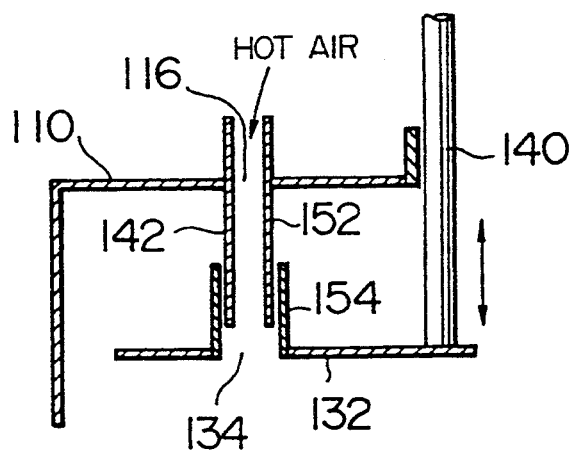
FIG. 3 is an enlarged cross-sectional view of a hot air introduction means of the treatment apparatus of FIG. 2.

As shown in FIG. 3, for example, the hot air introduction means 142 is constituted by a dual-tube construction having an inner tube 152 mounted on the chamber 110 and an outer tube 154 mounted on the seal plate 132, in which the tube 154 is slidable relative to the inner tube 152. In this case, the clearance between the inner and outer tubes 152 and 154 is made as small as possible so as to reduce the amount of leakage of the gas. The arrangement of the inner and outer tubes may be reversed.

Figure 4:
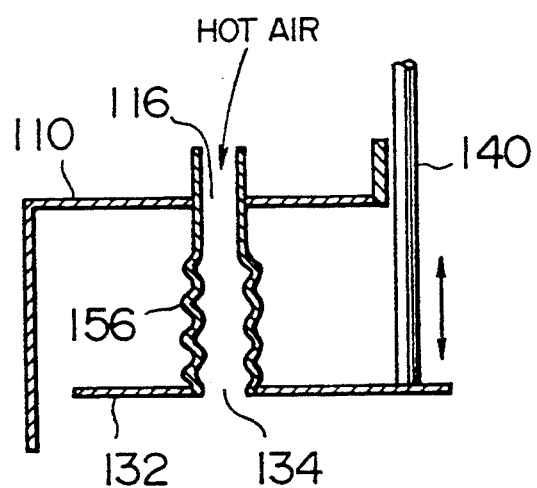
FIG. 4 is an enlarged cross-sectional view of a modified hot air introduction means.

As shown in FIG. 4, another example of hot air introduction means comprises a flexible tube 156 interconnecting the hot air inlet 116 of the heating chamber 110 and the hot air inlet port 134 of the seal plate 132.

Figure 5:
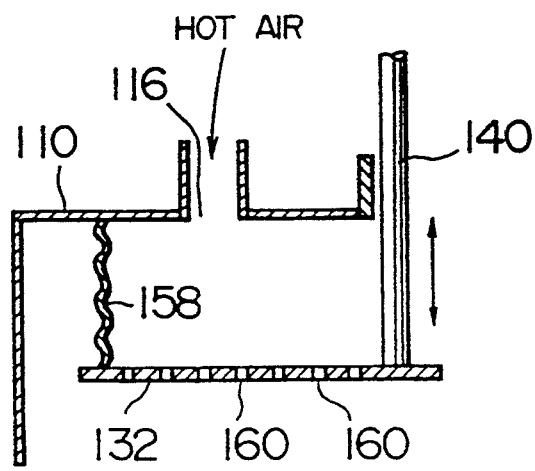
FIG. 5 is an enlarged cross-sectional view of another modified hot air introduction means.

As shown in FIG. 5, a further example of hot air introduction means comprises an expansible wall 158 of a generally cylindrical shape connected axially between the outer peripheral portion of the seal plate 132 and the upper wall of the heating chamber 110 disposed in substantially parallel opposed relation to the seal plate 132, in which case a number of small holes 160 are formed through that portion of the seal plate 132 disposed inside the expansible wall 158.

In the apparatus shown in FIG. 2, the medical wastes 144 to be treated are put into the waste receiving vessel 118, and then this vessel is introduced into the heating chamber 110. Then, the vessel 110 and the medical wastes are heated by the microwaves and the circulating hot air.

The circulating hot air is forcibly flowed only into the waste receiving vessel 118 to heat and sterilize and melt or soften the medical wastes. At the same time, the pressure of the hot air shrinks the medical wastes to reduce the volume thereof. The hot air within the waste receiving vessel 118, after heating the medical wastes, flows therefrom through the hot air passage holes 120, and is again heated and circulated.

Figure 6:
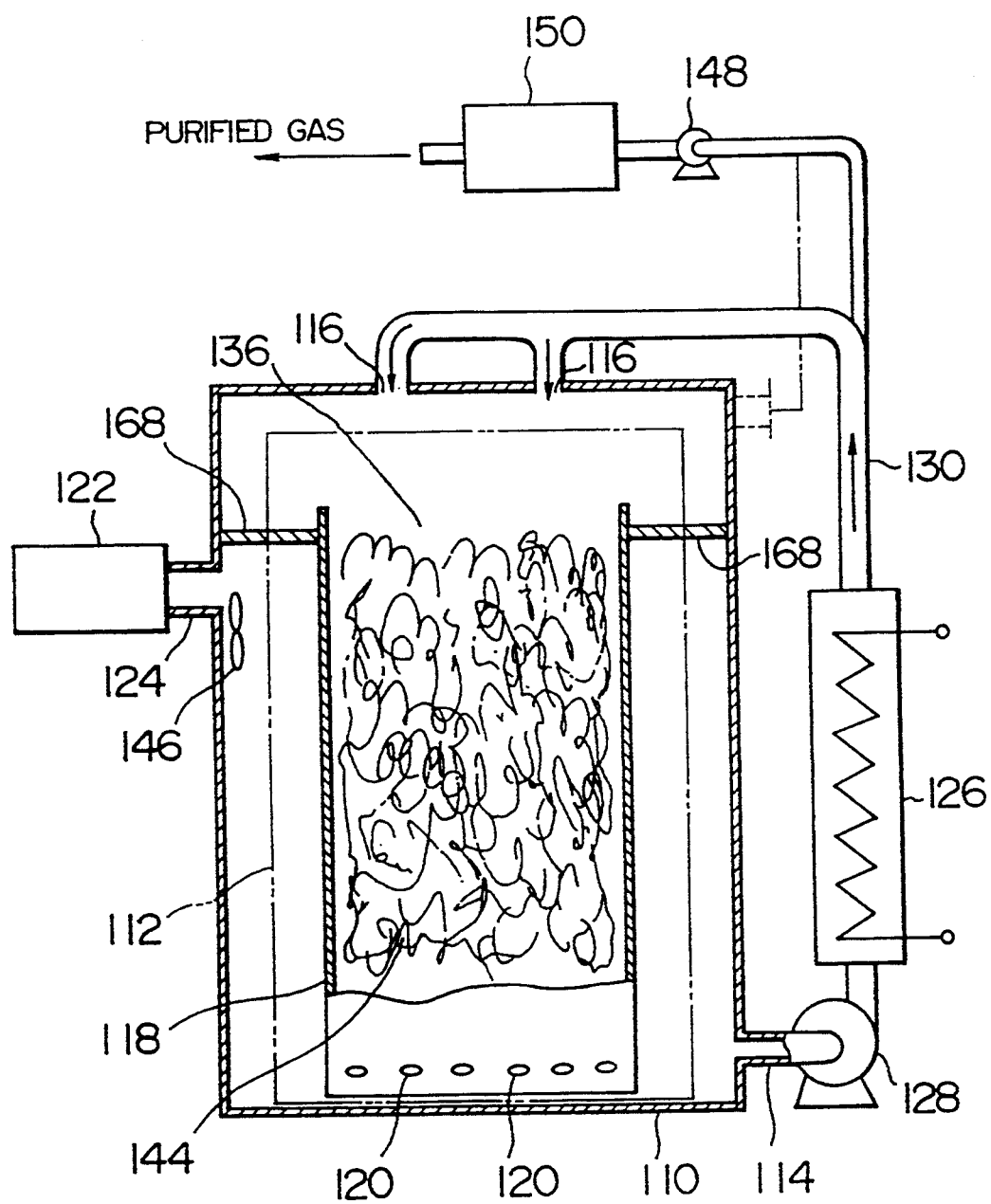
FIG. 6 is a vertical, partly cross-sectional view of a medical waste treatment apparatus according to a further embodiment of the invention.

In a further embodiment of the invention shown in FIG. 6, instead of providing the seal plate 132 and the seal plate moving device 138, there is provided a partition wall 168 of an annular shape which extends between a peripheral wall of a waste receiving vessel 118 and a peripheral wall of a heating chamber 110. With this arrangement, all of the hot air supplied to the heating chamber 110 are forcibly flowed into the waste receiving vessel 118. The partition wall 168 may be secured to either of the waste receiving vessel 118 and the wall of the heating chamber 110. The position of mounting of the partition wall 168 is not limited in so far as this partition wall is disposed above hot air passage holes 120, and also a plurality of such partition walls may be provided.

The other construction and operation of this embodiment are similar to those of the preceding embodiment of FIGS. 2 to 5.

In the embodiments shown in FIGS. 2 to 6, since all or most of the hot air is forced into the vessel, a good heat transfer is obtained, and the heating treatment time is shortened. Further, a local overheating can be prevented, and a uniform heating can be achieved, and therefore the temperature of the hot air required for achieving the intended sterilization effect can be lowered. In the case of treating the wastes containing polyvinyl chloride, the production of poisonous gas such as hydrogen chloride gas and etc. due to the local overheating can be prevented. Further, the shrinkage and volume-reduction of the wastes are promoted by the pressure of the forcibly-supplied hot air.

A further embodiment of the invention will be described with reference to FIG. 7.

Figure 7:
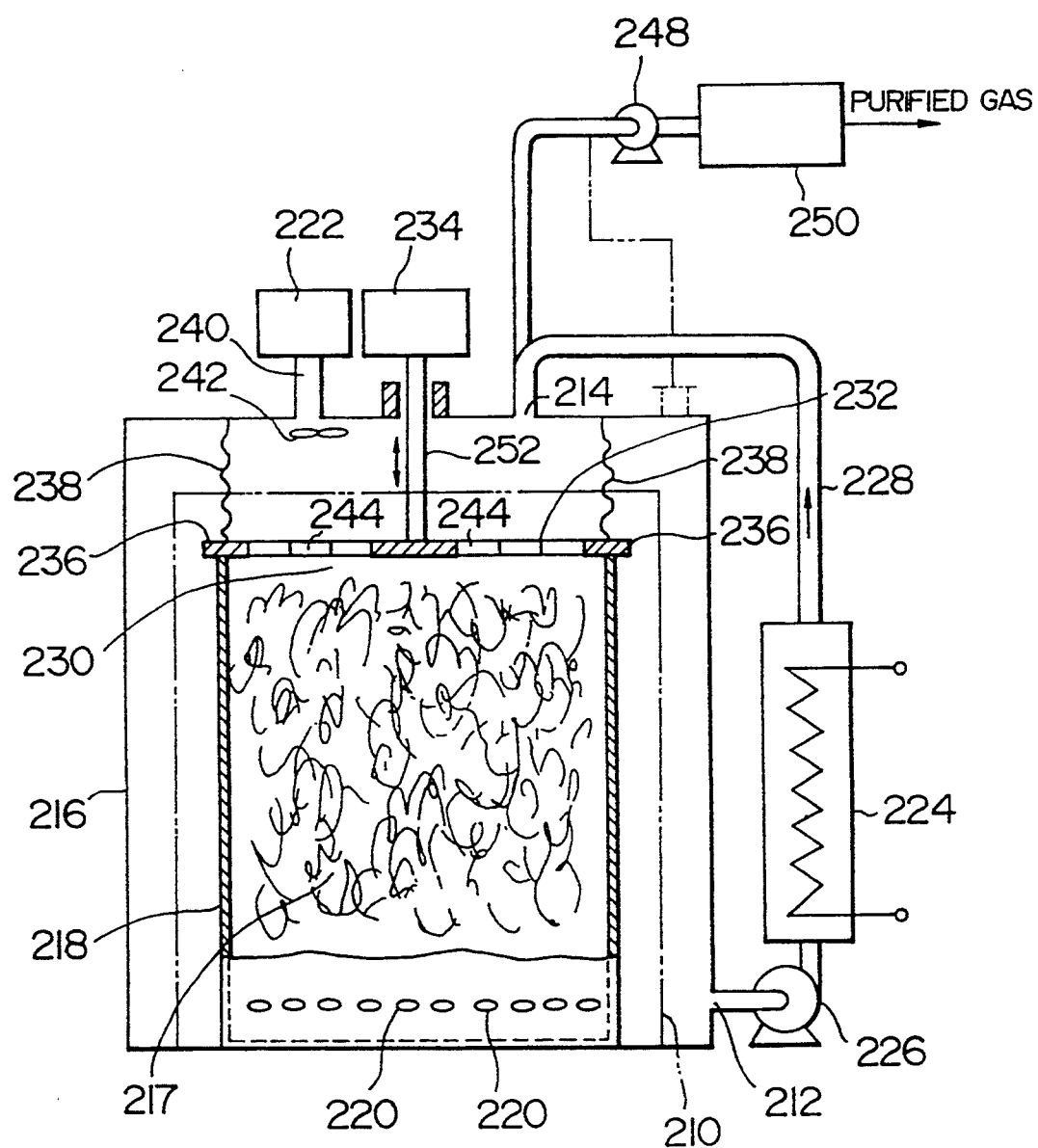
FIG. 7 is a vertical, partly cross-sectional view of a medical waste treatment apparatus according to a still further embodiment of the invention.

In FIG. 7, a heating chamber 216 which can be sealed has an introduction door 210, a hot air outlet 212 at its lower portion, and a hot air inlet 214 at its upper portion. A waste receiving vessel 218 for receiving wastes 217 to be treated is made of metal or the like so that microwaves can not transmit through or be absorbed by this vessel 218. The vessel 218 has a number of hot air passage holes 220 at its lower end portion. The hot air passage hole 220 has such a size as not to allow microwaves to pass therethrough. A microwave generating device 222 is connected to the heating chamber 216 via a waveguide 240. The waveguide 240 may be omitted, in which case the microwave generating device 222 is connected directly to the heating chamber 216. The hot air outlet 212 and the hot air inlet 214 of the heating chamber 216 are interconnected by a hot air circulating duct 228 having a hot air heater 224 and a hot air circulating blower 226. Instead of the hot air circulating duct 228, there can be used a double heating chamber structure (e.g. a double shell structure) having the function of a similar hot air flow passage.

A perforated plate 232 for closing an opening 230 of the waste receiving vessel 218 has vent holes 244 for passing the hot air therethrough. The vent hole 244 has such a size as to allow microwaves to pass therethrough. If the perforated plate is not made of metal or the like that is, this plate is made of a material to allow the microwaves to transmit therethrough, the vent hole 244 may have any size in so far as the required air flow rate is obtained. A perforated plate moving-device 234 for moving the perforated plate 232 upward and downward is connected to the perforated plate 232 via a piston 252. An expansible wall 238 of a generally cylindrical shape is connected axially between an outer peripheral portion 236 of the perforated plate 232 and the upper wall of the heating chamber 216 disposed in substantially parallel opposed relation to the perforated plate 232. The expansible wall 238 is made of metal or the like which does not allow the microwaves to transmit therethrough. Namely, it is necessary that the expansible wall 238, the wall of the waste receiving vessel 218, the outer peripheral portion 236 of the perforated plate 232, a choke structural portion (not shown) and a mounting plate for the choke structural portion should be made of metal or the like which does not allow the microwaves to transmit therethrough.

The waste receiving vessel 218 is put into the heating chamber 216, and the perforated plate 232 is moved by the perforated plate moving device 234 to a predetermined position, so that the outer peripheral portion 236 of the perforated plate 232 is brought into contact with the upper open end of the waste receiving vessel 218 so that the perforated plate 232 closes the opening 230 of the vessel 218. In order to detect the closing of the opening 230 by the perforated plate 232 so as to allow the subsequent application of the microwaves, a limit switch (not shown) or the like may be provided.

Reference numeral 242 denotes a stirrer fan for dispersing the microwaves uniformly, reference numeral 248 an induced draft fan, and reference numeral 250 an exhaust gas treatment device. The induced draft fan may be omitted.

The exhaust gas inlet side of the exhaust gas treatment device 250 is connected to the hot air circulating duct 228, but may be connected to the upper portion of the heating chamber as indicated by a broken line.

In the foregoing, although the medical waste treatment apparatus is disposed vertically, the apparatus, when in use, may be arranged horizontally.

For using the above apparatus, the medical wastes 217 to be treated are put into the waste receiving vessel 218, and then this vessel 218 is introduced into the heating chamber 216. Then, the vessel 218 and the medical wastes 217 are heated by the microwaves and the circulating hot air. At this time, the circulating hot air is forcibly flowed only into the vessel 218, and at the same time the microwaves are applied only to the interior of the vessel 218. By doing so, the wastes are efficiently heated and sterilized and melted or softened, and subsequently the wastes are easily reduced in volume by the pressure of the hot air, without the need for a pressing operation. The hot air within the waste receiving vessel 218, after heating the medical wastes, flows therefrom through the hot air passage holes 220, and is again heated and circulated.

In the above embodiment, the circulating hot air is forcibly flowed only into the waste receiving vessel, and the microwaves are applied only to the interior of the waste receiving vessel, and therefore the heat transfer efficiency is enhanced, and the heating treatment time is shortened. At the same time, a local overheating can be prevented, and a uniform heating can be achieved. Therefore, it is not necessary to raise the temperature of the hot air too much. In the case of treating wastes containing polyvinyl chloride, the generation of poisonous gas such as hydrogen chloride gas etc. due to the local overheating can be prevented. Further, the microwaves are applied only to the interior of the waste receiving vessel, and will not leak into the heating chamber, and therefore it is only necessary to take it into consideration that the door of the heating chamber can maintain the airtightness. This simplifies the construction. Further, the shrinkage and volume-reduction of the wastes are promoted by the pressure of the forcibly-supplied hot air.

As described above, in the medical waste treatment methods and apparatuses of the present invention, the medical wastes containing the plastic materials can be efficiently sterilized and reduced in volume.

What is claimed is:

1. Apparatus for treating medical wastes comprising:
   a sealable heating chamber having an introduction door, a hot air outlet and a hot air inlet;
   a waste receiving vessel in said heating chamber, said waste receiving vessel having hot air passage holes;
   a microwave generating device connected to said heating chamber;
   a hot air circulating portion interconnecting said hot air outlet and said hot air inlet of said heating chamber, said hot air circulating portion having a hot air heater and a hot air circulating blower;
   a sealing plate provided at an opening of said waste receiving vessel so as to seal said waste receiving vessel, said sealing plate having a hot air inlet port;
   a sealing plate moving device for moving said sealing plate relative to said opening; and
   hot air introduction means interconnecting said hot air inlet of said heating chamber and said hot air inlet port of said sealing plate.

2. Apparatus according to claim 1, in which said hot air introduction means is constituted by a double-tube structure comprising a pair of inner and outer tubes slidable relative to each other.

3. Apparatus according to claim 1, in which said hot air introduction means is constituted by a flexible tube.

4. Apparatus according to claim 1, in which said hot air introduction means is constituted by an expansible wall of a generally cylindrical shape connected axially between an outer peripheral portion of said sealing plate and a wall of said heating chamber disposed in generally parallel opposed relation to said sealing plate, said hot air inlet port having a number of small holes formed through that portion of said sealing plate disposed inside of said expansible wall.

5. Apparatus according to claim 1, in which an exhaust gas treatment device for removing poisonous gas components, combustion gas and odor components contained in exhaust gas is connected to one of said sealable heating chamber and said hot air circulating portion.

6. Apparatus according to claim 5, in which said exhaust gas treatment device adsorbs and removes acid gas, composed mainly of hydrogen chloride gas, at a reaction adsorption temperature of 150° to 200° C. at a space velocity of 500 to 5000 $hr^{-1}$, using a reaction adsorbent selected from the group consisting of oxides and hydroxides of the elements in groups I, II and VIII of the periodic table, said exhaust gas treatment device effecting the oxidative decomposition of the combustible gas and the odoriferous gas at a reaction temperature of 200° to 450° C. at a space velocity of 500 to 40,000 $hr^{-1}$, using Pt and/or Pd catalyst.

7. Apparatus according to claim 5, in which an exhaust gas treatment device for removing poisonous gas components, combustion gas and odor components contained in exhaust gas is connected to one of said sealable heating chamber and said hot air circulating portion.

8. Apparatus for treating medical wastes comprising:
   a sealable heating chamber having a medical waste introduction door, a hot air outlet and a hot air inlet;
   a waste receiving vessel in said heating chamber, said waste receiving vessel having hot air passage holes;
   a microwave generating device connected to said heating chamber;
   a hot air circulating portion interconnecting said hot air outlet and said hot air inlet of said heating chamber, said hot air circulating portion having a hot air heater and a hot air circulating blower; and
   a partition wall extending between a peripheral wall of said waste receiving vessel and a peripheral wall of said heating chamber.

9. Apparatus according to claim 8, in which an exhaust gas treatment device for removing poisonous gas components, combustion gas and odor components contained in exhaust gas is connected to one of said sealable heating chamber and said hot air circulating portion.

10. Apparatus for treating medical wastes comprising:
    a sealable heating chamber having a medical waste introduction door, a hot air outlet and a hot air inlet;
    a waste receiving vessel in said heating chamber, said waste receiving vessel having hot air passage holes;
    a microwave generating device connected to said heating chamber;
    a hot air circulating portion interconnecting said hot air outlet and said hot air inlet of said heating chamber, said hot air circulating portion having a hot air heater and a hot air circulating blower;
    a perforated plate for closing an opening of said waste receiving vessel;
    a perforated plate moving device for moving said perforated plate relative to said opening; and
    an expansible wall of a generally cylindrical shape connected axially between an outer peripheral portion of said perforated plate and a wall of said heating chamber disposed in substantially parallel opposed relation to said perforated plate.

* * * * *